(12) United States Patent
Arab et al.

(10) Patent No.: US 11,061,018 B2
(45) Date of Patent: *Jul. 13, 2021

(54) COMPOSITIONS AND METHODS FOR DISEASE DIAGNOSIS USING SINGLE CELL ANALYSIS

(71) Applicant: Pattern Bioscience, Inc., Austin, TX (US)

(72) Inventors: Nicolas Arab, Austin, TX (US); Ross Johnson, Austin, TX (US)

(73) Assignee: PATTERN BIOSCIENCE, INC., Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/656,962

(22) Filed: Oct. 18, 2019

(65) Prior Publication Data
US 2020/0256854 A1     Aug. 13, 2020

Related U.S. Application Data

(63) Continuation of application No. 15/833,629, filed on Dec. 6, 2017, now Pat. No. 10,488,404, which is a
(Continued)

(51) Int. Cl.
*C12Q 1/04*     (2006.01)
*G01N 33/50*    (2006.01)
*G01N 15/14*    (2006.01)
*C12Q 1/18*     (2006.01)
*G01N 21/64*    (2006.01)
*G01N 33/58*    (2006.01)
*G01N 15/10*    (2006.01)

(52) U.S. Cl.
CPC ........... *G01N 33/5091* (2013.01); *C12Q 1/04* (2013.01); *C12Q 1/18* (2013.01); *G01N 15/1463* (2013.01); *G01N 21/6428* (2013.01); *G01N 33/5011* (2013.01); *G01N 33/582* (2013.01); *G01N 2015/1006* (2013.01); *G01N 2015/1406* (2013.01); *G01N 2015/1481* (2013.01); *G01N 2201/0621* (2013.01); *G01N 2800/26* (2013.01)

(58) Field of Classification Search
CPC ........................................................ C12Q 1/04
See application file for complete search history.

(56) References Cited

U.S. PATENT DOCUMENTS 5,501,959 A    3/1996  Lancaster et al.
6,174,670 B1   1/2001  Wittwer et al.
(Continued)

FOREIGN PATENT DOCUMENTS

WO    WO 2003/025113    3/2003

OTHER PUBLICATIONS

Boedicker et al., "Detecting Bacteria and determining their susceptibility to antibiotics by stochastic confinement in nanoliter droplets using plug-based microfluidics," *Lab Chip*, 8(8):1265-1272, (2008).
(Continued)

*Primary Examiner* — Rosnne Kosson
(74) *Attorney, Agent, or Firm* — Norton Rose Fulbright US LLP

(57) ABSTRACT

Certain embodiments of the invention are directed to evaluating and identifying cells by recording and interpreting a time-dependent signal produced by unique cell respiration and permeability attributes of isolated viable cells.

19 Claims, 13 Drawing Sheets

Related U.S. Application Data continuation of application No. 15/466,377, filed on Mar. 22, 2017, now Pat. No. 9,851,345.

(60) Provisional application No. 62/407,311, filed on Oct. 12, 2016.

(56) References Cited

U.S. PATENT DOCUMENTS

| | | | |
|---|---|---|---|
| 6,673,578 | B1 | 1/2004 | Uemori et al. |
| 6,990,290 | B2 | 1/2006 | Kylberg et al. |
| 8,622,987 | B2 | 1/2014 | Ismagilov et al. |
| 8,895,255 | B1 | 11/2014 | Goldberg et al. |
| 9,851,345 | B1 | 12/2017 | Arab et al. |
| 2005/0084923 | A1 | 4/2005 | Mueller et al. |
| 2006/0259249 | A1 | 11/2006 | Sampath et al. |
| 2010/0227767 | A1 | 9/2010 | Boedicker et al. |
| 2019/0218497 | A1 | 7/2019 | Boedicker et al. |

OTHER PUBLICATIONS

Chen et al., "Characterization of Dye Leakage in Microfluidic Droplets," 17$^{th}$ International Conference on Miniaturized Systems for Chemistry and Life Science, pp. 1947-1949, (2013).

International Search Report and Written Opinion issued in International Patent Application No. PCT/IB17/56326, dated Mar. 28, 2018.

Invitation to Pay Additional Fees issued in International Application No. PCT/IB2017/56326, dated Feb. 12, 2018.

Scheler et al., "Fast Quantification of Aerobic Bacteria Using Droplet Microfluidics," 19$^{th}$ International Conference on Miniaturized Systems for Chemistry and Life Science, pp. 398-400, (2015).

Scheler et al., "Dodecylresorufin (C12R) Outperforms Resorufin in Microdroplet Bacterial Assays," ACS Appl. Mater. Interfaces, 8:11318-11325, (2016).

Shemesh et al., "Stationary nanoliter droplet array with a substrate of choice for single adherent/nonadherent cell incubation and analysis," PNAS, 111(31):11293-11298, (2014).

Office Action issued in corresponding European Patent Application No. EP 17 86 0574 dated Apr. 30, 2020.

Amselem et al, "Universal microfluidic platform for bioassays in anchored droplets", Lab on a Chip, vol. 16, No. 21, Jan. 1, 2016, pp. 4200-4211.

Kaushik et al, "Rapid assessment of bacterial vitality and antibiotic susceptibility via high-throughput picoliter-droplet single-cell assay", 19$^{th}$ International Conference on Miniaturized Systems for Chemistry and Life Sciences (MicroTAS 2015), Apr. 1, 2016, pp. 531-533.

Liu et al, "High-throughput screening of antibiotic-resistant bacteria in picodroplets", Lab on a Chip, vol. 16, No. 9, Apr. 1, 2016, pp. 1636-1643.

Theophel et al, "The importance of growth kinetic analysis in determining bacterial susceptibility against antibiotics and silver nanoparticles", Frontiers in Microbiology, vol. 5, Nov. 10, 2014.

Van Belkum et al, "Next-Generation Antimicrobial Susceptibility Testing", Journal of Clinical Microbiology, vol. 51, No. 7, Jul. 1, 2013, pp. 2018-2024.

U.S. Appl. No. 61/052,490, filed May 12, 2008, Boedicker, et al.

two-dimensional droplet array easy to image/video over time

Actual image of E. coli in droplets

COMPOSITIONS AND METHODS FOR DISEASE DIAGNOSIS USING SINGLE CELL ANALYSIS

PRIORITY CLAIM

This application is a continuation of U.S. application Ser. No. 16/656,962 filed Oct. 18, 2019, which is a continuation of U.S. application Ser. No. 15/833,629 filed Dec. 6, 2017, which is a continuation of U.S. application Ser. No. 15/466,377 filed Mar. 22, 2017 (now U.S. Pat. No. 9,851,345) which claims priority to U.S. Application No. 62/407,311, filed Oct. 12, 2016, each of which is incorporated herein by reference in its entirety.

TECHNICAL FIELD

This disclosure relates generally to cellular biology and more particularly to compositions and methods for rapid and sensitive identification of disease-causing cells and the rapid and sensitive characterization of their response to the drugs used to treat them.

BACKGROUND

In various instances, Disease-Causing Cells (DCCs) are found in quantities below the limit-of-detection of conventional analytical techniques. Thus, methods for identifying DCCs and characterizing their response to treatment typically require either multiplication of the target cells and/or target-dependent amplification of the target cells' molecular contents and/or products, depending on the application.

Due to high sensitivity compared to other techniques, nucleic acid amplification (e.g., PCR-based) tests (NATs) have become the preferred method for fast pathogen identification. Culture based methods are the currently preferred method for antimicrobial susceptibility testing because the methods assess the microbial phenotype, providing high clinical validity.

NATs require complicated sample workflow steps which usually include cell lysis followed by nucleic acid concentration step that also removes PCR inhibitors from the samples. Cell lysis creates an asymmetry in the requirements for nucleic acid extraction efficiency. Mycobacteria and fungi, for example, possess a very thick cell wall compared to gram-negative bacteria and thus are far more difficult to lyse, usually requiring a mechanical lysis step to efficiently disrupt their cell wall. Consequently, NATs that utilize simple chemical lysis methods often lack sensitivity for these tougher pathogens. Furthermore, cell lysis reagents are extremely inhibitory to PCR reaction because they are designed to efficiently denature proteins and PCR utilizes proteins to perform the amplification reaction. Cell lysis, therefore, introduces the need for highly efficient wash steps to remove lysis reagents from the extracted nucleic acid. In addition, NATs require expensive assay development methods because they rely on pathogen-specific reporter molecules (primers and probes) that must be designed specifically for each target. Each NAT must therefore include an expensive molecular R&D process which involves primer/probe design and screening for each target.

Furthermore, if a NAT assay includes more than one target (multiplex assay), requiring more than one reporter species (primer pair), the different target and/or reporter species can interact nonspecifically with one another, causing either false positives when the reporter amplifies nonspecifically against the other reagents or false-negatives when the target amplification reaction is inhibited by a non-specific interaction with another species. Consequently, this limits how many targets can be identified within a single NAT. This becomes particularly relevant with the issue of drug resistance because, in the case of gram-negative bacteria and mycobacteria, there are numerous mutations (each mutation being a target) indicative of resistance. NATs can only interrogate a small fraction of those mutations within a single test. In addition, the genes that reside in an organism's genotype may not always contribute to the phenotype. Therefore, genotypic information often portrays an inaccurate or incomplete picture of a pathogen's phenotypic response. Methicillin-resistant *Staphylococcus aureus* (MRSA), for example, often do not express the mecA gene that confers resistance. Therefore, when it comes to the clinically important determination of whether the pathogen causing an infection is susceptible to a particular drug NATs have low clinical validity.

NATs that include two or more targets (multiplexed) cannot simultaneously quantify those targets accurately and precisely. This is because the same nonspecific interactions between reporter species described above also cause variances in the PCR signal output and quantitative PCR relies on reproducible reaction results in order to correlate the generated amplification curves to the initial target concentration. This is a significant limitation because it prevents the use of multiplex NATs for the diagnosis of infections from non-sterile fluids since humans are often colonized by the same pathogens that can cause an infection. In non-sterile fluids, therefore, the number of pathogens present in the clinical sample (the pathogen load) is what determines whether a bacterial species is causing an infection or "peacefully" colonizing the fluid. For example, in order to definitively diagnose the source of a pneumonia infection from a bronchioscopic specimen (e.g., bronchooalveolar lavage (BAL)) the pathogen load for any bacteria present in the sample must exceed $10^3$ CFU/mL to be considered the source of an infection. Similarly, for urine specimens the threshold is $10^5$ CFU/mL.

In addition, quantitative culture methods encounter problems identifying polymicrobial infections when one of the infecting pathogens is a fastidious organism (an organism that has a complex nutritional requirement and typically only grows under specific conditions) and the other is not. The non-fastidious organism will often drown out the fastidious organism on a culture plate and conceal its presence in the specimen. This is particularly problematic because many of the drug-resistant microbes are fastidious non-fermenting rods (gram-negatives).

Thus, there remains a need for additional methods and apparatus for identifying and characterizing disease causing cells (DCCs) in a fast and/or efficient manner.

SUMMARY

Certain aspects of the methods described herein can be practiced using an integrated workflow and analysis that can be automated and performed on disposable cartridge providing integrated testing without having to utilized one or more kits to perform sample preparation prior to analysis. The methods described can be implemented as a single step automated process. The compositions and methods described herein address the various problems associated with the current methods for identifying and characterizing DCCs. DCCs are defined herein as either host cells, such as malignant or disease-associated cells of the host from which the sample is taken (e.g., cancer cells), or acquired cells (e.g., fungal or bacterial), which include any microflora associated with, involved in, implicated in, or indicative of a disease or pathology. Such diseases include, but are not limited to cancer and infections.

Embodiments of the invention are directed to methods that identify pathogens by recording and interpreting a time-dependent signal produced by unique cellular metabolism, respiration, and/or permeability attributes of isolated cells. In certain aspects of the current invention does not require lysis or washing. As used herein, metabolism refers to the set of life-sustaining chemical transformations or processes within a cell. The three main purposes of metabolism are the conversion of food/fuel to energy to run cellular processes; the conversion of food/fuel to building blocks for proteins, lipids, nucleic acids, and some carbohydrates; and the elimination of nitrogenous wastes. Respiration as referred to herein is cellular respiration, a set of metabolic reactions and processes that take place in a cell or organisms to convert biochemical energy from nutrients into adenosine triphosphate (ATP), and then release waste products. Furthermore, since intact cells are used, only whole cells need to be manipulated rather than nucleic acid molecules, which are much more difficult manipulate due to their small size and propensity for charge-based interactions with different materials. Furthermore, the cells can be incubated at a single temperature, typically a relatively low temperature in the range of 25 to 45° C., obviating the need for thermal cycling equipment required for most NATs, which reduces cost and workflow complexity of the currently described invention. Advantageously, by avoiding high temperature steps, the invention avoids significant issues that can arise with fluid evaporation and/or bubbles that can disrupt the integrity of the reaction and/or the fluorescent readout.

Furthermore, certain methods described herein utilize a single, universal reporter molecule for all target cells. As used herein a reporter is a molecule, peptide, protein, or other compound that varies in fluorescence emission, absorption, and/or reflectance in relation to a variation in environment or condition, such as reduction-oxidation (redox) state. Thus, unlike NATs, where each reporter molecule is designed to respond only to one particular target, the universal reporter in the described methods responds to all the targets (e.g., DCCs) in a target specific manner, that is the response can be different for each target using the same reporter. In certain instances it is the "shape" or waveform of the reporter signal over time that changes or is unique to a target rather than the reporter molecules used to generate the presence or absence of a signal. Thus, it is the "system" that acts like a probe rather than the individual reporter molecules. With a universal reporter, assay development becomes, in certain instances, effectively a software R&D exercise because only data storage and analysis are changed between targets. This offers a significant advantage because software changes are much faster and cheaper to implement, augment, and test compared to molecular or chemistry changes. In some cases, it may be necessary to change the cell suspension formulation to include certain drugs or nutrients, formulation changes that are much faster and simpler to implement and optimize than molecular design changes.

The methods described herein produce metabolic, respiratory, or drug-susceptibility profiles that can be used to identify or phenotype a target cell in a sample. Specifically, just as this method uses a mammalian cell's or microbial cell's unique metabolism, respiration, and/or permeability characteristics to distinguish between different cellular and microbial species, those same characteristics can be used to determine whether the cell or microbe is susceptible to a particular compound, cytotoxic compound, or antimicrobial, since a compound or an effective drug will alter the cellular metabolism, respiration, and/or permeability characteristics. In certain aspects methods of the invention can interrogate the interactions of a compound(s) or conditions on a cell, be it (i) a normal cell for determining toxicity of a compound or condition, or (ii) a pathogenic or disease-related cell for determining therapeutic efficacy of a compound or condition. This method can account for all resistance mechanisms that may confer resistance to a particular cell and, therefore, offers higher clinical validity than that of NATs, which can only account for a fraction of the resistance mechanism. This is why, despite being much faster, NATs have not been able to replace culture-based methods for drug-susceptibility testing. NATs typically produce a result in about an hour whereas existing culture-based drug-susceptibility methods typically require over 48 hrs.

The currently described methods produce phenotypic susceptibility results at significantly faster turn-around-times (<4 to 6 hrs) than culture-based phenotypic methods. The increase in speed compared to culture is accomplished, in part, by the rapid signal concentration made possible at sub-nanoliter volumes which are orders of magnitude smaller than the milli- and microliter volumes typically used by other methods. Put simply: confinement of each cell or microbe into sub-nanoliter droplets enables reporters (e.g., fluorescent molecules) to be rapidly detected or rapidly concentrate to detectable levels. And since this method can detect single cells, the method is as sensitive as NATs which are more sensitive the culture methods. Thus, the described methods offers the analytical validity of NATs combined with the clinical validity of culture based methods.

In the method described herein, individual cells or microbes are isolated or partitioned into separate droplets, enabling quantification to become the simple matter of counting those droplets that produced a signal indicating the presence of a target cell or microbe. The shape or change of the reporter signal over time (e.g., a waveform), which is one of the characteristics relied upon for pathogen identification and characterization, is orthogonal to the method for quantifying the number of pathogens—one does not affect the other. Thus, accurate and precise multiplexed identification and quantification is accomplished simultaneously.

Finally, the reporter or cell viability reagents used in the invention are inexpensive compared to the materials used in NATs. And because of their simple structure, they can be easily lyophilized and solubilized. A variety of reporters may be used with the systems and methods disclosed herein. For example, the at least one small molecule metabolic reporter can be a fluorophore, a protein labeled fluorophore, a protein comprising a photooxidizable cofactor, a protein comprising another intercalated fluorophore, a mitochondrial vital stain or dye, a dye exhibiting at least one of a redox potential, a membrane localizing dye, a dye with energy transfer properties, and/or a pH indicating dye. In a further aspect the reporter can be or include a resazurin dye, a tetrazolium dye, coumarin dye, an anthraquinone dye, a cyanine dye, an azo dye, a xanthene dye, an arylmethine dye, a pyrene derivative dye, a ruthenium bipyridyl complex dye or a derivative thereof. As used herein, "derivative" is understood to mean a chemically modified form of a dye that maintains some of the detection characteristics, e.g., fluorescent sensitivity to redox state, of the compound from which it is derived. Certain embodiments utilize a resazurin-based dye which is very inexpensive compared to PCR reagents, such as expensive enzymatic components.

Some compounds or antimicrobials are only effective against certain cells or microbes (indeed, this is why, in the absence of definitive drug-susceptibility information, it is important to identify the causative pathogen to guide therapy), for example, a microbe's response to a particular antimicrobial aids in identifying the microbe. This sensitivity is one reason bacterial culture methods utilize antibiotics in the growth media to identifying the growing bacteria. Certain embodiments of the invention provide a method for rapid and sensitive identification of disease-causing cells and the rapid and sensitive characterization of their response to the drugs used to treat them. In certain aspects, target cells are re-suspended with a reporter (e.g., a resazurin-based dye), poising agents or test compounds (optional), and cell nutrients (e.g., growth media), the suspension is compartmentalized into droplets and organized into a two-dimensional array where they are incubated and their fluorescence is monitored over time using an imaging system. Each viable DCC contained within a droplet will influence the environment or conditions in the drop which in turn affects the reporter. For instance, a viable DCC contained within a droplet can irreversibly reduce resazurin into highly fluorescent resorufin, causing the droplets to emit fluoresce when excited. Subsequently, if the environmental oxidation-reduction (redox) potential dips below a certain threshold, the resorufin is reversibly reduced to hydroresorufin, which is a non-fluorescent molecule. If the redox potential rises above the same certain threshold, the hydroresorufin is oxidized back to resorufin and fluoresces again. Thus, the amount of fluorescence emitted from a droplet can undulate over time depending on the changing environment or conditions (e.g., redox potential) of the droplet. Because cells have different metabolic or redox characteristics, cells will produce characteristic fluorescent undulations (signatures) that can be used to identify which cell type is in the droplet. A characteristic signature can also be generated by stressing the cell with an environmental stressor or condition, such as an antimicrobial drug or potential therapeutic. By combining the information contained within one or more of these signatures, single cells contained within each droplet can be identified and characterized.

In one embodiment, the cells in a test sample are divided into two populations, one population (the test population) includes an environmental stressor or test condition, and in the other population (the control population) the environmental stressor or test condition is excluded. The two populations are observed over time. The cells in the test sample may be identified by population characteristics and/or from the signatures in a control population. Identification may be further aided by the signatures generated in the test population, but the primary purpose of the test population is to characterize the response of the cells to the environmental stressor or test condition by comparing the test population signatures to the control signatures.

Particular embodiments are directed to methods for identifying and characterizing a disease causing cell (DCC) in a sample or diagnosing a disease associated with a disease causing cell. The methods can comprise (a) contacting a sample suspected of containing one or more target disease causing cells (DCCs) with at least one reporter (e.g., a viability or reporter dye) forming a sample mixture; (b) partitioning the sample mixture into partitions comprising at most one target DCC or natural DCC aggregate per partition; (c) incubating the partitions for a period of time at a specified temperature or series of temperatures; (d) monitoring optical characteristics of the partitions during the incubation time; (e) constructing a waveform (signal over time) for each partition based on the optical characteristics over time; and (f) evaluating the sample using information provided by partition waveforms. As used herein, a natural DCC aggregate is an association of two or more cells having the same phenotype (i.e., a homogenous aggregate), the association of which is not readily dissociated by the processing conditions. In certain instances the DCC aggregate is an aggregate of microbes having the same phenotype.

In certain aspects the partitions are droplets in an immiscible fluid. Upon mixing of the target-containing solution and the immiscible fluid, they form phases—an aqueous drop or partition, which holds the target material in solution, and a non-aqueous phase made up of the immiscible fluid. The immiscible fluid can be a fluorocarbon comprising a fluorosurfactant or hydrocarbon oils such as mineral oil, or silicone oils. In particular aspects the droplets can be between 0.1 pL and 10 nL. In a further aspect the droplets are at least, at most, or about 0.1. 0.5, 1, 5, 10, 20, 30, 40, 50, 60, 70, 80, 90, or 100 pL to 200, 300, 400, 500, 600, 700, 800, 900, or 1000 pL, including all values and ranges there between. In certain aspects the droplets are about 40 to 300 pL. The methods can further comprise arranging the droplets in a two-dimensional array. In certain aspects the two-dimensional array is a static two-dimensional array. Partitioning of the sample can be done by Laplace pressure gradients or by using shear stress methods, as well as other methods for drop or partition formation.

Monitoring of the optical characteristics of the partitions can be performed using a detector, such as a camera or the like. In certain aspects the optical characteristics include fluorescence of the partition(s). In certain aspects the monitoring of the optical characteristics of the partitions further comprises illuminating or exposing the partition with electromagnetic radiation, such as light. In certain aspects the electromagnetic radiation comprises an excitation wavelength that is compatible with the reporter, i.e., illuminating or irradiating a partition with an appropriate source. In certain aspects the source provides light including an excitation wavelength of 500, 525, 550, 575, 600, 625, 650, 675, to 700 nm, including all values and ranges there between. The source will be selected so that the electromagnetic radiation excites one or more reporter in the samples, e.g., dyes or other compounds. In particular aspect the light source can be a light emitting diode (LED).

Reporters can include a "viability dye" or "reporter dye", the viability or reporter dye is a moiety that detects changes in the environment surrounding an isolated cell due to a cell's viability, respiration, or metabolic activity; or is a detectable protein that is expressed under specific conditions (e.g., green fluorescent protein or luciferase). In certain aspects a cell can be transfected or engineered to express a reporter protein. The reporter can be detected using any method known in the art appropriate to the reporter employed, for example light emission or absorbance of a fluorophore or a colorimetric dye. In certain instances, the signal from the reporter is detected by optical microscopy, camera, or other detector/sensor as appropriate. In certain aspects the reporter is a fluorescent dye. In certain aspects the reporter is resazurin, a resazurin-based dye, or a dye that is a derivative of or structurally related to resazurin (7-Hydroxy-3H-phenoxazin-3-one 10-oxide). Resazurin is a non-toxic, cell permeable compound that, in its oxidized state, is blue in color and virtually non-fluorescent. When in contact with living cells, resazurin is reduced to resorufin, a compound that is red in color and highly fluorescent, and can be detected fluorimetrically or colorimetrically. Metabolic activity of viable cells continuously convert resazurin to resorufin, increasing the overall fluorescence and color of the media surrounding cells. A resazurin-based dye is a dye that contains a resazurin structure in addition to other modifying groups. In other aspects a viability dye is tetrazolium, a tetrazolium-based dye, or a dye that is a derivative of or structurally related to tetrazolium. A tetrazolium-based dye is a dye that contains a tetrazolium moiety and may contain other modifying groups that do not disrupt the five membered tetrazolium ring.

In certain aspects the incubating of the partitions is at a constant temperature (isothermal). In other aspects the temperature can be controlled and can be stepped or ramped up using a particular interval or rate, such as stepping up from 25 to 37° C. or increasing at a rate of 2 to 10° C. per minute. In still other aspects temperature can be decreased at a particular interval or rate, such as decreasing at an interval of 5 to 10° C. or a rate of 2 to 10° C. per minute. In various aspects the temperature(s) are in the range of 20 to 45° C., 30 to 40° C., or 35 to 38° C., including all values and ranges there between. In certain aspects partitions are incubated at 37° C.

In particular aspects the partitions comprise a single cell, microbe, or cellular or microbial aggregation. In a further aspect the partition may contain 2, 3, 4, or more cell or microbe types. The methods can further comprise classifying a microbe by species, genus, family, order, class, phylum, kingdom, or a combination thereof. The classification can be based on the characteristics of one or more waveforms under one or more conditions. In certain aspects the microbe is a bacteria. Certain aspects of the invention can include classifying the bacteria by gram-stain group or other classification criteria recognized for microbes, including bacteria. In certain instances a partition may contain more than one target type (species, genus, etc.) but that an environmental stressor or condition may kill all but one target type, which can be identified using its signature or waveform.

The methods can further comprise dividing the sample into a control sample and at least one test sample prior to partitioning. Each test sample can be treated or processed in a manner that differs from the control. In certain aspects at least one test sample is contacted with a stressor, cytotoxic, anticancer, antimicrobial compound or condition. In certain aspects individual test samples can be exposed to different concentrations compounds or variations in conditions. In other aspects, a test sample can be exposed to a variety of temperatures, environments, or chemicals that may or may not alter the phenotype of the cells contained in the test sample. In certain aspects a DCC is a pathologic or pathogenic cell, such as a cancer cell.

The methods include evaluating the sample (control and test samples) using the partition waveform (i.e., signal detected over time). In certain aspects evaluating includes comparing the partition waveform to a library of stored or predetermined waveforms (e.g., waveform reference).

Certain embodiments are directed to methods for detecting and characterizing DCCs, such as microbes or cancer cells, in a sample comprising (a) contacting a sample comprising microbes with a reporter, e.g., a viability dye, forming a sample mixture; (b) dividing the sample mixture into at least two portions or samples that include a control sample and at least one test sample; (d) introducing a test compound/substance or an antimicrobial drug to the at least one test sample; (e) partitioning each of the control sample and at least one test sample into partitions forming control sample partitions and test sample partitions, wherein the partitions comprise at most one target microbe or a natural aggregation of microbes; (f) incubating the partitions over time at a specific temperature or temperatures; (g) monitoring optical characteristics of the partitions during the incubation time, wherein the optical characteristics include the amount of optical signal produced by interaction of the reporter with the microbe in the partition; (h) constructing an optical signal waveform for each partition resulting in a partition waveform; (i) classifying the microbe within each partition using the partition waveform shape; and (j) comparing partition waveforms between the control sample partition waveforms and the test sample partition waveforms and assessing test compound/substance or antimicrobial drug susceptibility based partition waveform comparison. In certain aspects a test compound can include a small molecule, peptide, a nanoparticle, or a protein. In still other instances a test substance can include bacteriophage and other engineered therapeutics. In other aspects the test compound/substance can be a therapeutic identified as a therapy or engineered as a therapy for other disease conditions, such as cancer (e.g., chemotherapeutic or anti-cancer compound or substance).

Another primary application of this invention is towards the diagnosis and treatment of diseases such as cancer. Cancer diagnosis is very similar to infectious disease diagnosis in that disease causing cells can mutate rapidly and can develop resistance to the drugs used to treat them. Furthermore, cancer cells exhibit different morphological, metabolic, and respiratory characteristics than healthy cells. Specifically, cancer cells are known to exhibit different oxidation-reduction characteristics from healthy cells. Furthermore, cancer cells are often much larger than healthy cells which also influences the amount of fluorescence generated during respiration. Because, certain aspects of this method are sensitive to oxidation-reduction (redox) changes that occur during cellular respiration, those differences, as well as others, may be used to distinguish cancer cells from healthy cells. In addition, cancer cells often bypass apoptosis pathways and are therefore able to remain viable for longer periods of time when they no longer reside in specific tissues. In this case, the cellular respiration would last longer for cancer cells compared to healthy cells, which could be observed as signal accumulates for longer periods of time for cancer cells compared to healthy cells. In certain aspects the waveforms for normal cells will differentiate them from pathogenic or cancer cells.

As used herein, the term "partition" refers to a volume of fluid (e.g., liquid or gas) that is a separated portion of a bulk volume. A bulk volume may be partitioned into any suitable number (e.g., $10^2$, $10^3$, $10^4$, $10^5$, $10^6$, $10^7$, etc.) of smaller volumes or partitions. Partitions may be separated by a physical barrier or by physical forces (e.g., surface tension, hydrophobic repulsion, etc.). Partitions generated from the larger volume may be substantially uniform in size (monodisperse) or may have non-uniform sizes (polydisperse). Partitions may be produced by any suitable manner, including emulsion, microfluidics, and microspray methods. One example of partitions are droplets.

As used herein, the term "droplet" refers to a small volume of liquid which is immiscible with its surroundings (e.g., gases, liquids, surfaces, etc.). A droplet may reside upon a surface, be encapsulated by a fluid with which it is immiscible, such as the continuous phase of an emulsion, a gas, or a combination thereof. A droplet is typically spherical or substantially spherical in shape, but may be non-spherical. The shape of an otherwise spherical or substantially spherical droplet may be altered by deposition onto a surface. A droplet may be a "simple droplet" or a "compound droplet," wherein one droplet encapsulates one or more additional smaller droplets. The volume of a droplet and/or the average volume of a set of droplets provided herein is typically less than about one microliter, for example droplet volume can be about 1 µL, 0.1 µL, 10 pL, 1 pL, 100 nL, 10 nL, 1 nL, 100 fL, 10 fL, 1 fL, including all values and ranges there between. The diameter of a droplet and/or the average diameter of a set of droplets provided herein is typically less than about one millimeter, for example 1 mm, 100 µm, 10 µm, to 1 µm, including all values and ranges there between. Droplets may be formed by any suitable technique, including emulsification, microfluidics, etc., and may be monodisperse, substantially monodisperse (differing by less than 5%), or polydisperse.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In the following discussion and in the claims, the terms "including" and "comprising" are used in an open-ended fashion, and thus should be interpreted to mean "including, but not limited to . . . ." Also, the term "link" or "points to," and forms thereof, are intended to mean either an indirect or direct connection. Thus, if a first component links to a second component, that connection may be through a direct connection or through an indirect connection via other components and connections.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

For a more complete understanding of the present disclosure, and the advantages thereof, reference is now made to the following descriptions taken in conjunction with the accompanying drawings, in which.

DETAILED DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The invention generally relates to methods for disease diagnosis using single-cell analysis. The following sections discuss general considerations for test samples, compartmentalization/partitioning, cell viability and viability or reporter dyes, disease-causing cell aggregates/aggregation of microbes, signal detection, and multiplexing.

Figure 1:
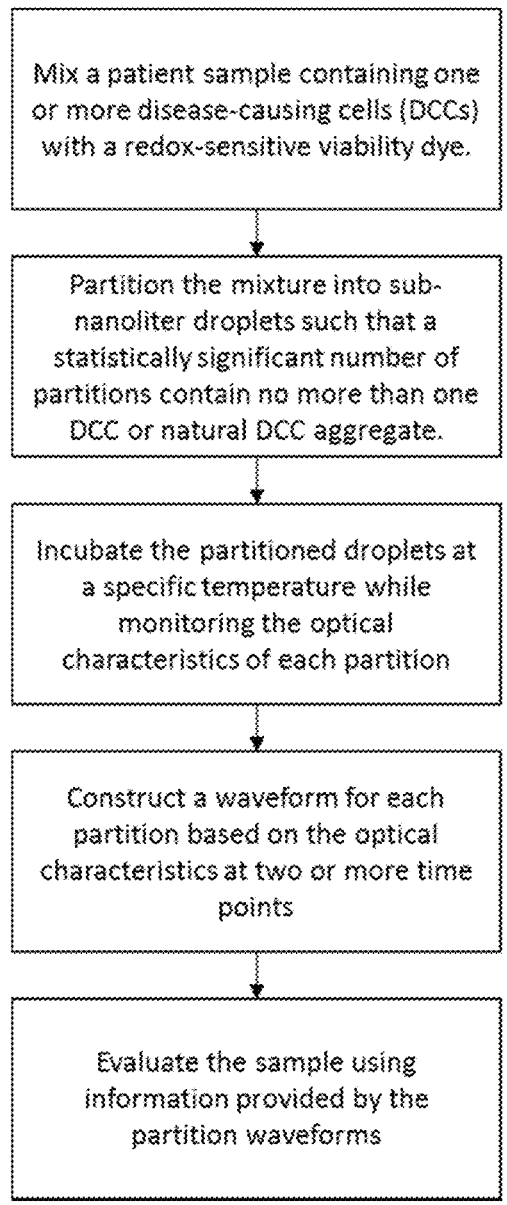
FIG. 1 is a schematic of a preferred embodiment of the invention applied to generally to disease causing cells.
Figure 2:
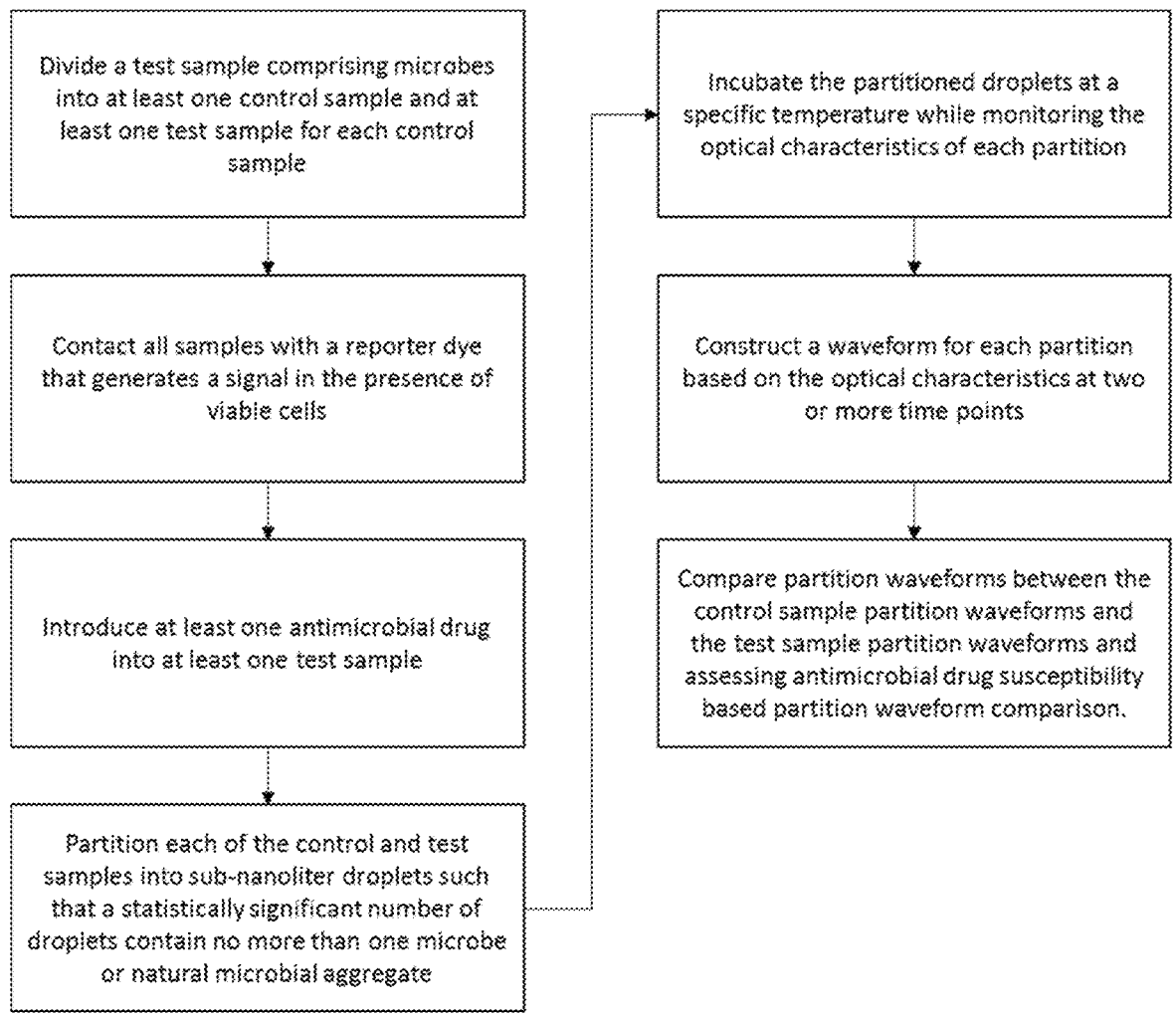
FIG. 2 is a schematic of a preferred embodiment of the invention which as a method pathogen identification and antimicrobial susceptibility testing by monitoring the fluorescence over time of individual cells and/or monoclonal cell clusters isolated in subnanoliter droplets with a redox-sensitive viability dye.

A general scheme is shown in FIG. 1. A test sample comprising at least one target cell is combined with a viability or reporter dye and partitioned into droplets such that a statistically significant number of droplets contain no more than one target cell or aggregation of cells (some microbial species tend to aggregate into cell clusters or chains). In a preferred embodiment, a viability or reporter dye will be reduced from a non-fluorescent molecule to a fluorescent molecule in the presence of a viable cell and then further reduced to a non-fluorescent molecule if the redox potential in the droplet drops below a certain amount, typically −100 mV. The fluorescent signature generated in each droplet is monitored over time and used to identify and characterize the cell contained within. Further details on the processes of the invention are provided below.

Test Sample. Target cells in the test sample include bacteria, fungi, plant cells, animal cells, or cells from any other cellular organism. The cells may be cultured cells or cells obtained directly from naturally occurring sources. The cells may be obtained directly from an organism or from a biological sample obtained from an organism, e.g., from sputum, saliva, urine, blood, cerebrospinal fluid, seminal fluid, stool, and tissue. Any tissue or body fluid specimen. In one embodiment the test sample includes cells that are isolated from a biological sample comprising a variety of other components, such as non-target cells (background cells), viruses, proteins, and cell-free nucleic acids. The cells may be infected with a virus or another intracellular pathogen. The isolated cells may then be re-suspended in different media than those from which they were obtained. In one embodiment the test sample comprises cells suspended in a nutrient medium that enables them to replicate and/or remain viable. The nutrient media may be defined media with known quantities or all ingredients or an undefined media where the nutrients are complex ingredients such yeast extract or casein hydrolysate, which contain a mixture of many chemical species of unknown proportions, including a carbon source such as glucose, water, various salts, amino acids and nitrogen. In one embodiment, the target cells in the test sample comprise pathogens and the nutrient media comprises a commonly used nutrient broth (liquid media) for culturing pathogens such as lysogeny broth, nutrient broth or tryptic soy broth. In any embodiment the media may be supplemented with a blood serum or synthetic serum to facilitate the growth of fastidious organisms.

Figure 10:
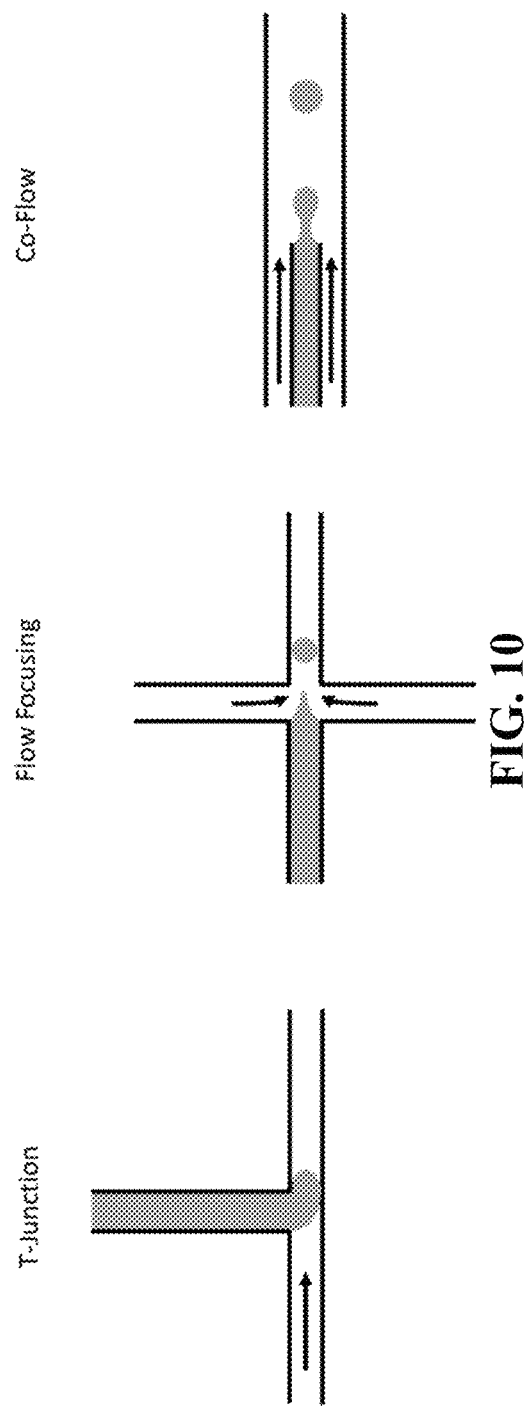
FIG. 10 illustrates one method of using shear stress for droplet generation.
Figure 11:
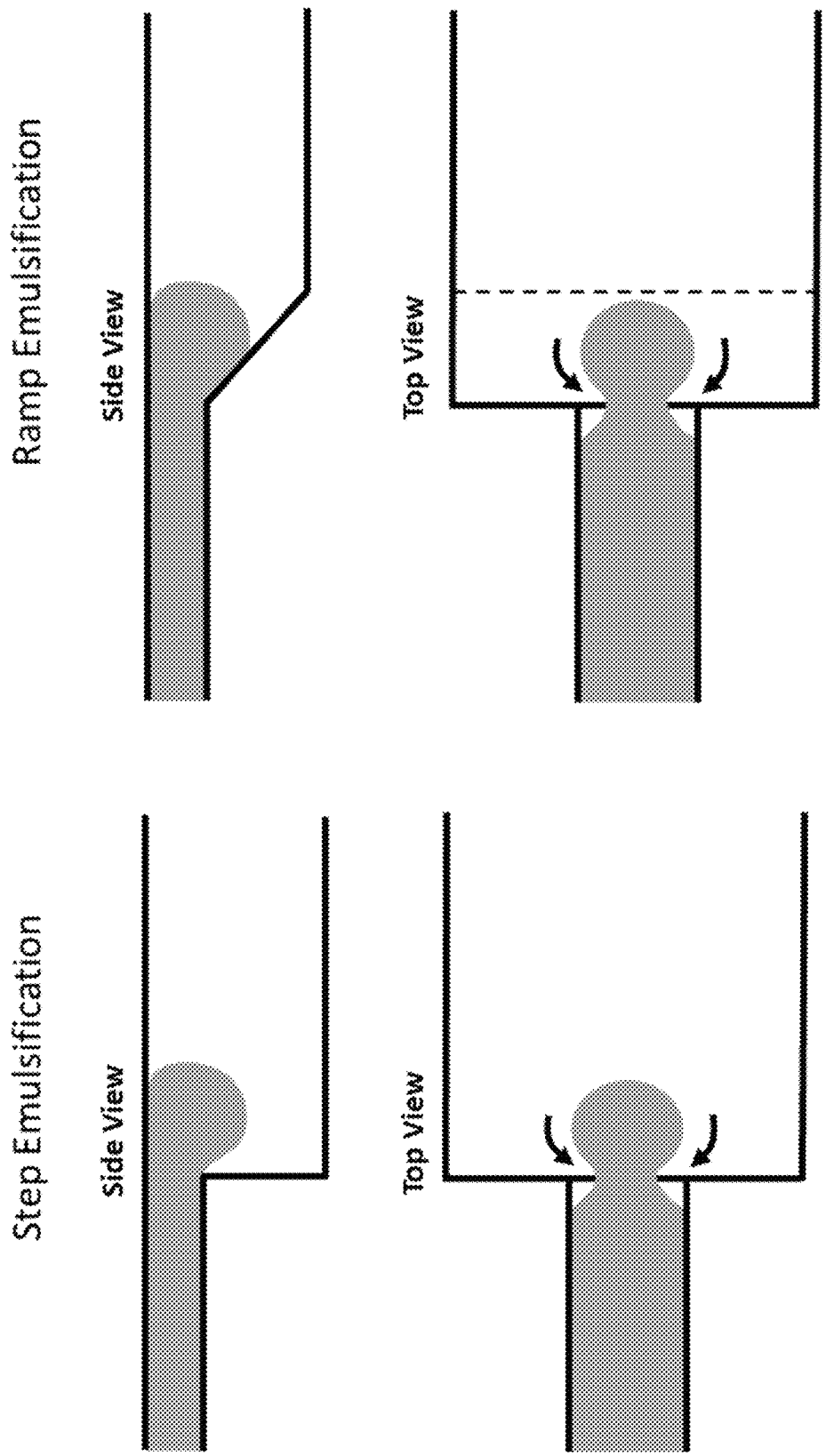
FIG. 11 illustrates two methods of using Laplace pressure gradients for droplet generation.
Figure 12:
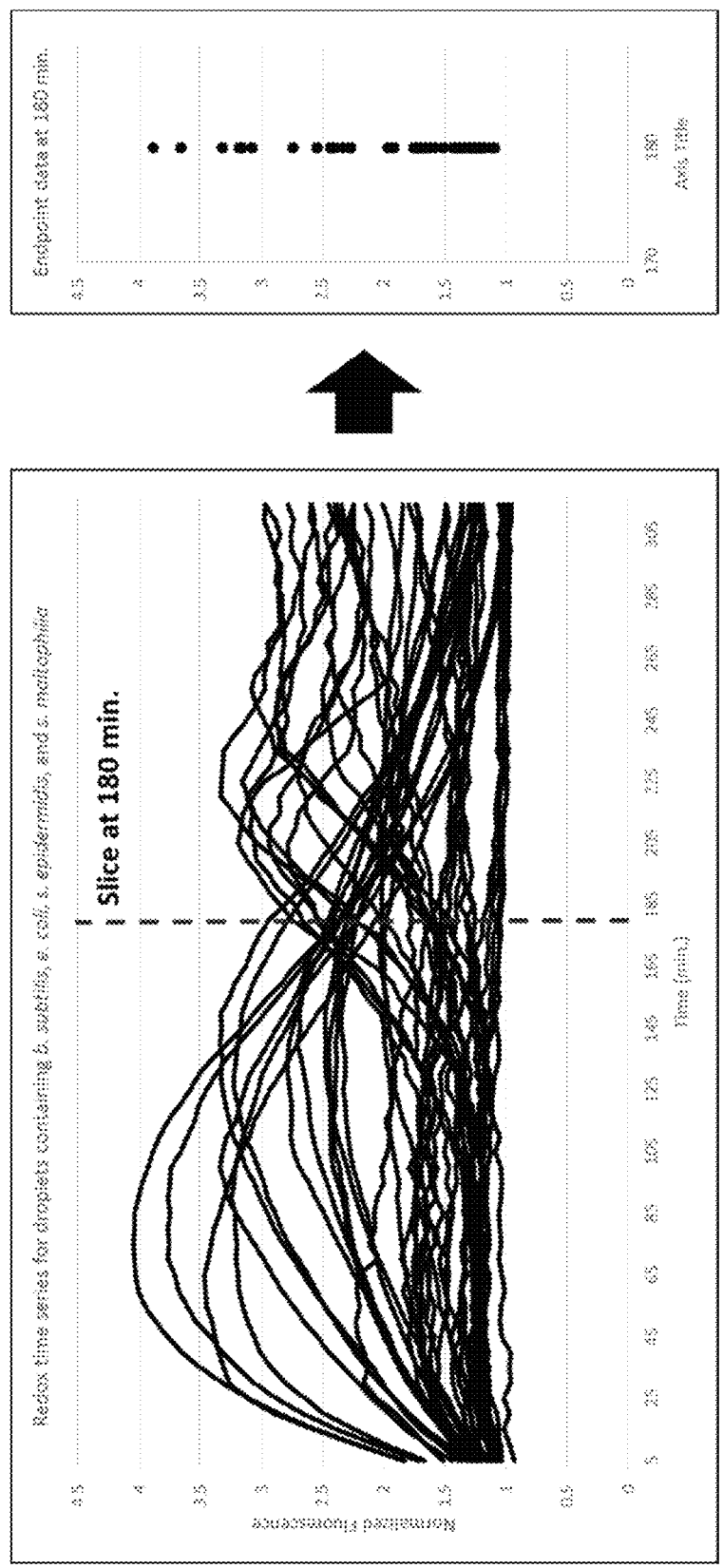
FIG. 12 illustrates the distinction between waveform monitoring as compared to a discreet value at particular time. At pico-liter volumes, where the redox potential causes fluorescence to vary depending on the bacterial species, traditional endpoint analysis does not provide distinguishable viability information.
Figure 13:
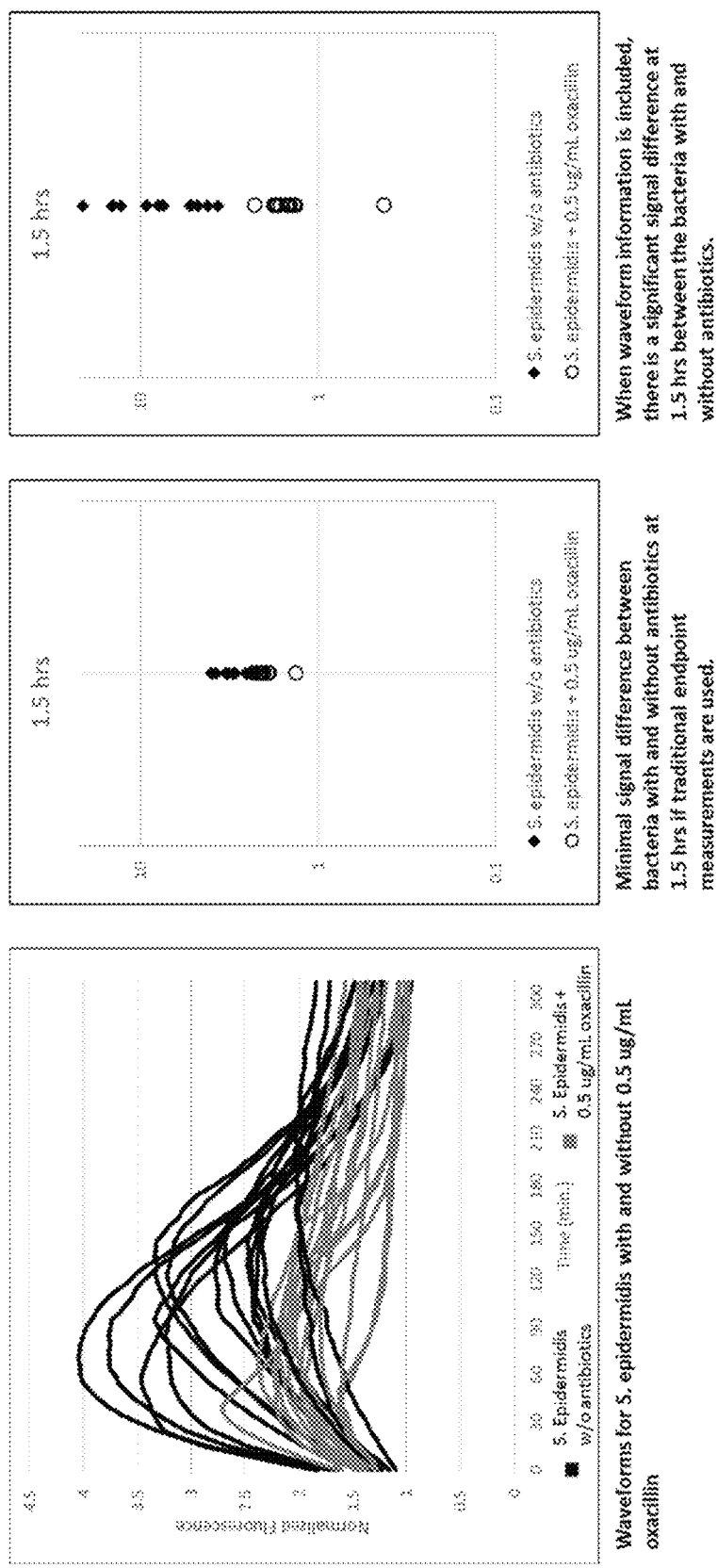
FIG. 13 illustrates that waveform information provides an increased sensitivity when detecting drug-susceptibility.
Figure 14:
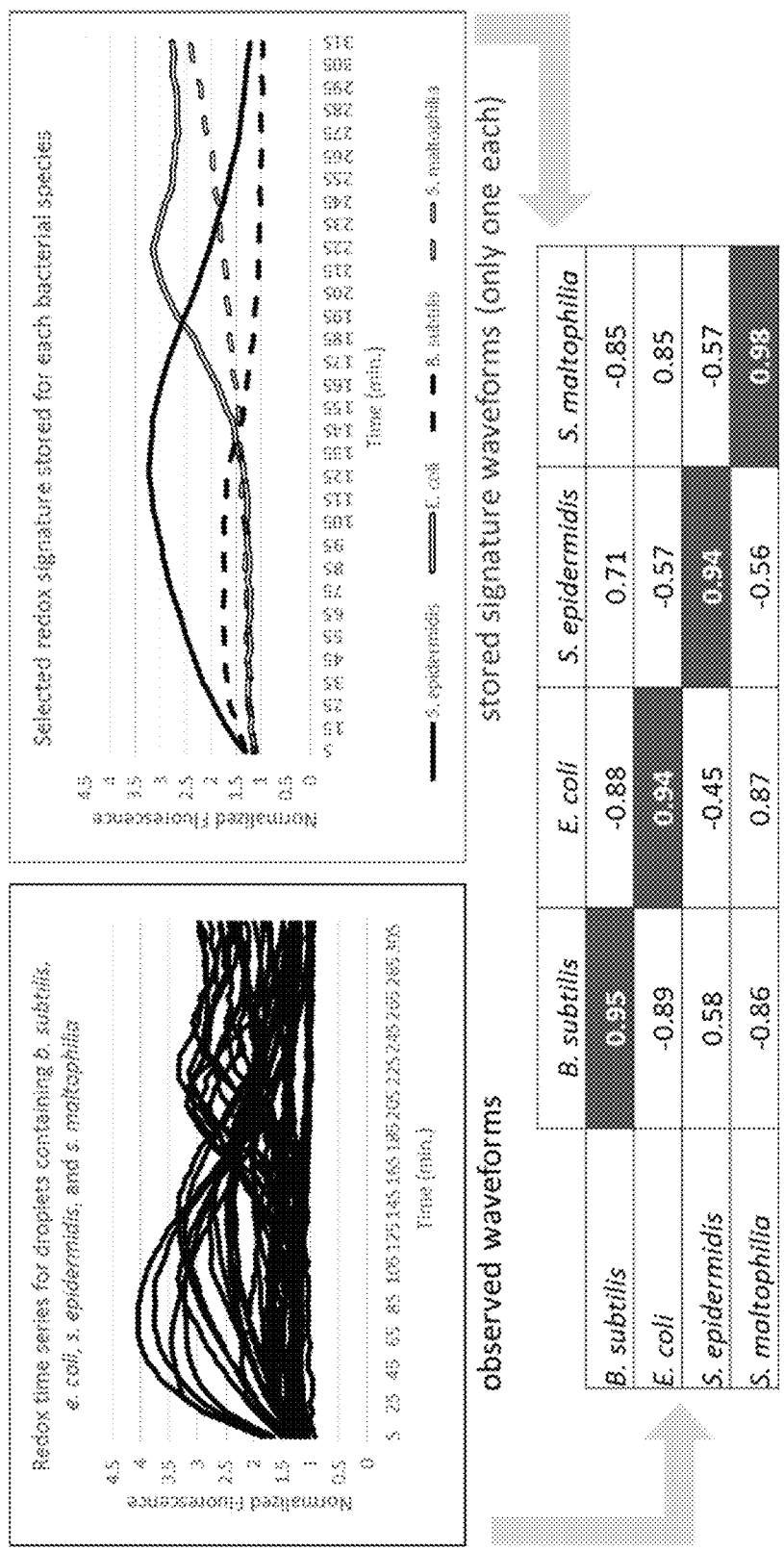
FIG. 14 illustrates stored waveforms representing four bacterial species and their correlation to observed waveforms from the same species (median correlation coefficient) and, thus, can be used to identify the bacteria that generated the observed waveforms. Stored waveforms also correlate well according to gram stain gram (*B. subtilis* and *S. epidermidis* are gram positives, *E. coli* and *S. maltophilia* are gram negatives).

Compartmentalization/Partitioning. The methods of the invention involve combining a test sample comprising at least one target cell with a viability or reporter dye and then partitioning the test sample into droplets such that no droplet contains more than one target cell or cell aggregates. The number of droplets can vary from hundreds to millions depending on the application and droplet volumes can also vary between 1 pL to 100 nL depending on the application, but preferably between 25-500 pL. The methods described herein are compatible with any droplet generation method. Exemplary methods for droplet generation are shown in FIG. 10 and FIG. 11. While the methods for droplet formation differ, all the methods disperse an aqueous phase, the test sample in this case, into an immiscible phase, also referred to as the continuous phase, so that each droplet is surrounded by an immiscible carrier fluid. In one embodiment the immiscible phase is an oil wherein the oil comprises a surfactant. In a related embodiment, the immiscible phase is a fluorocarbon oil comprising a fluoro-surfactant. An important advantage to using a fluorocarbon oil is that it is able to dissolve gases relatively well and it is biologically inert. Thus, the fluorocarbon oil used in the methods described herein comprises solubilized gases necessary for cell viability.

One non-limiting example of partition formation is by using Laplace pressure gradients (see, for example, Dangla et al., 2013, *PNAS* 110(3):853-58). Laplace pressure is the differential pressure between the inside and outside of a curved surface, such as the difference in pressure between the inside and outside of a droplet. An aqueous phase containing cells or microbes can be introduced into a device having a reservoir of a continuous phase (i.e., immiscible fluid) forming an aqueous "tongue" in an appropriate device. The device can incorporate height variation(s) into a microchannel that subject the immiscible interfaces to a difference in curvature between the portion of the aqueous phase that has not encountered the height variation and the portion of the aqueous phase downstream of the height variation. As the aqueous phase flows through the height variation, a critical curvature is reached for the portion of the aqueous phase downstream of the height variation beyond which the two portions cannot remain in static equilibrium, breaking of the aqueous phase into a droplet, as the downstream portion detaches from the tongue formed by introduction of the aqueous phase into a continuous phase, the size of the drops being determined by the device geometry. The height variation can be accomplished with a single step change in the height of a microchannel (step emulsification), multiple steps (multi-step emulsification), and a ramp or similarly gradual gradients of confinement.

Reporters. A variety of reporters may be used with the systems and methods disclosed herein. For example, the at least one small molecule metabolic reporter can be a fluorophore, a protein labeled fluorophore, a protein comprising a photooxidizable cofactor, a protein comprising another intercalated fluorophore, a mitochondrial vital stain or dye, a dye exhibiting at least one of a redox potential, a membrane localizing dye, a dye with energy transfer properties, a pH indicating dye. In a further aspect the reporter can be or include a resazurin dye, a tetrazolium dye, coumarin dye, an anthraquinone dye, a cyanine dye, an azo dye, a xanthene dye, an arylmethine dye, a pyrene derivative dye, a ruthenium bipyridyl complex dye or derivatives thereof. Certain embodiments utilize a resazurin-based dye. Cell viability dyes, which are also included in the term reporter used herein, are used as analysis reagents to identify and characterize individual cells or pathogens encapsulated within droplets. Viability dyes have been used since the 1950's for cell viability purposes. However, these reagents are typically employed in samples that are significantly greater than 1 microliter in volume and/or are used as an endpoint assay to indicate the presence of viable cells. Aspects of the invention use a viability dye in droplets that are between 1 pL and 100 nL, and more specifically 25-500 pL. In the method described here the optical signal generated by the viability dye is concentrated by the small droplet volume and measured and recorded over an incubation time. In droplets containing viable cells, this results in an optical signature that is rapidly generated and has information about the characteristics of the cell encapsulated within the droplets. Combined with an environment stressor, such as an antimicrobial or cytotoxic drug, an additional signature can be generated by monitoring the optical signal of the droplets containing a cell over time. The optical signatures from the cell with and without the environmental stressor can be used to determine the identity and/or characteristics of the cell. Furthermore, the differences between the optical signatures obtained from a species of cells exposed to a drug compared to the optical signatures for same species of target cells that are not exposed to the drug can be used to determine the phenotypic drug resistance profile for the target cells obtained from a test sample. Because these signatures are generated from individual cells encapsulated in droplets, they represent information about the individual characteristics of each cell as opposed to an average characteristic of a population of cells that is generated from a bulk sample containing many cells.

Figure 6:
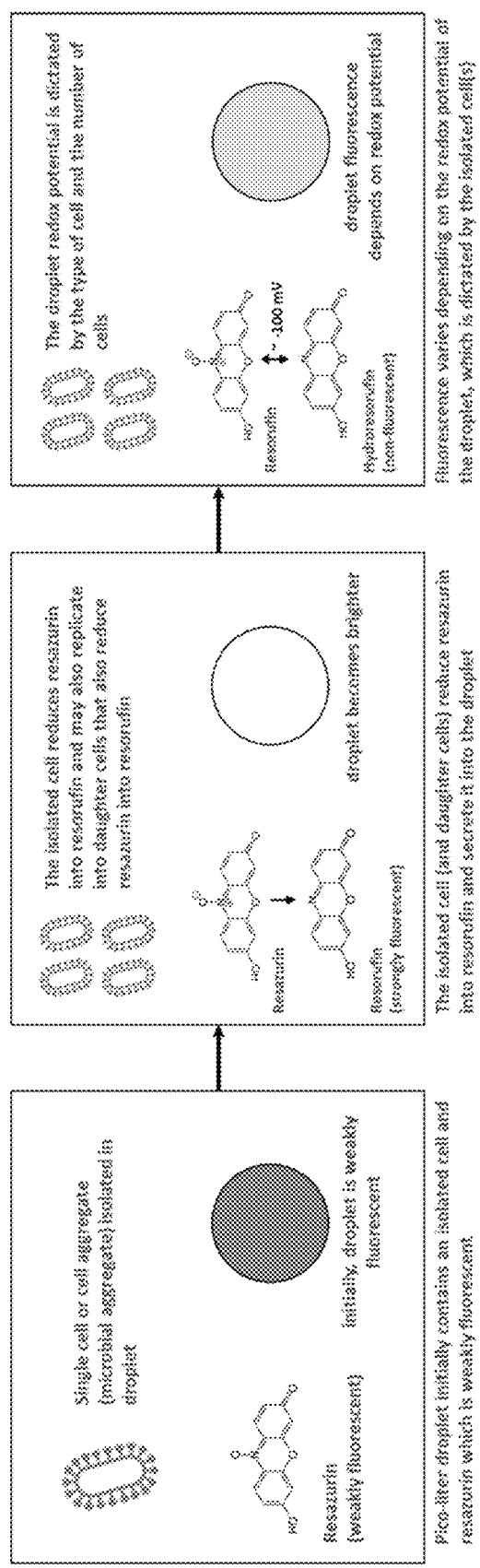
FIG. 6 is a schematic providing one explanation of as to fluorescence variation according to the redox environment established by an isolated cell.
Figure 7:
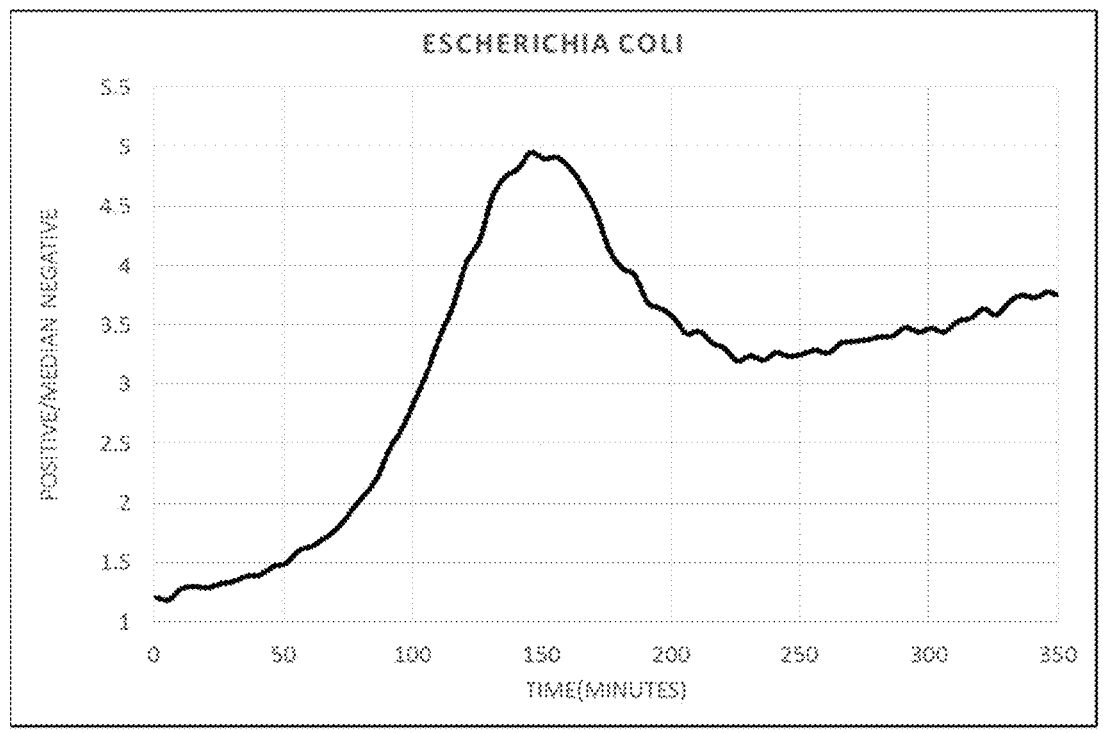
FIG. 7 illustrates a waveform derived from an *E. coli* cell in a 268 pL droplet.

The methods of the invention are compatible with any viability or reporter dye that can be used with live cells (does not require cell lysis). In a preferred embodiment the viability dye is a resazurin-based dye or derivative thereof. When blue, non-fluorescent resazurin is irreversibly reduced to pink and highly fluorescent resorufin (FIG. 6) it produces a fluorescent signal and a colorimetric shift (from blue to pink). In a preferred embodiment, the fluorescence is used because it offers better sensitivity over colorimetric signal changes. The limited-diffusion confinement within a sub-nanoliter volume of secreted fluorescent molecules quickly concentrates to detectable signal levels and is then detected by the methods described below. Furthermore, resorufin is reversibly reduced to non-fluorescent hydroresorufin (FIG. 6) if the redox environment dips below a particular redox threshold, usually around −100 mV. The combination of irreversible reduction from resazurin to resorufin and the reversible reduction of resorufin to hydroresorufin and oxidation of hydroresorufin back to resorufin depending on the redox potential of the droplet are what create the unique fluorescence signature over time in droplets that are small enough volume such that redox changes occur quickly in the presence of a single cell or cell aggregate. Examples of commercially available resazurin-based dyes are: AlamarBlue™ (various), PrestoBlue™ (Thermo Fisher Scientific), Cell-titer Blue™ (Promega), or Resazurin sodium salt powder. Dyes that are structurally related to resazurin and can be also be used in the method are: 10-acetyl-3,7-dihydroxyphenoxazine (also known as Amplex Red™) 7-ethoxyresorufin, and 1,3-dichloro-7-hydroxy-9,9-dimethylacridine-2 (9H)-one (DDAO dye). In alternate embodiments dyes that rely on tetrazolium-reduction, such as formazan dyes, can be used as the cell viability indicator. Examples include INT, MTT, XTT, MTS, TTC or tetrazolium chloride, NBT, and the WST series.

Cell (DCC) Aggregates. A preferred application of the invention is towards the diagnosis of microbial infections by identifying the microbes causing the infection and whether or not they are resistant to antimicrobial drugs. Thus, in this application, the DCCs can be single-celled microbes. Some bacteria, however, aggregate naturally into clusters or chains. In these cases, some droplets may comprise an aggregate of cells of the same microbial species (homogenous aggregate) rather than a single microbe. In these cases, the shape of the curve may be affected by the number of cells in the aggregate. However, the stored signature waveforms and call logic that are used to classify the compartmentalized cells can account for such aggregates the same way they can account for single cells. Furthermore, if the embodiment includes antimicrobial susceptibility testing the mixture comprising the antimicrobial drug will exhibit the same cell aggregation characteristics as the mixture that excludes the antimicrobial drug and the comparison will still be accurate. Therefore, while the method of the invention generally comprises isolation of single-cells in each droplet, it necessarily accommodates the case of a single cell species in a homogenous aggregate isolated in the droplet rather individual cells. In the case of cancer disease diagnosis, the target DCCs typically do not aggregate if they are circulating tumor cells. If the cancer cells are obtained from tissue, the tissue is typically disintegrated into individual cells prior to analysis. Therefore, each droplet will contain at most one cell; however, in some instances a cancer aggregate may also be analyzed using the described methods.

Figure 3:
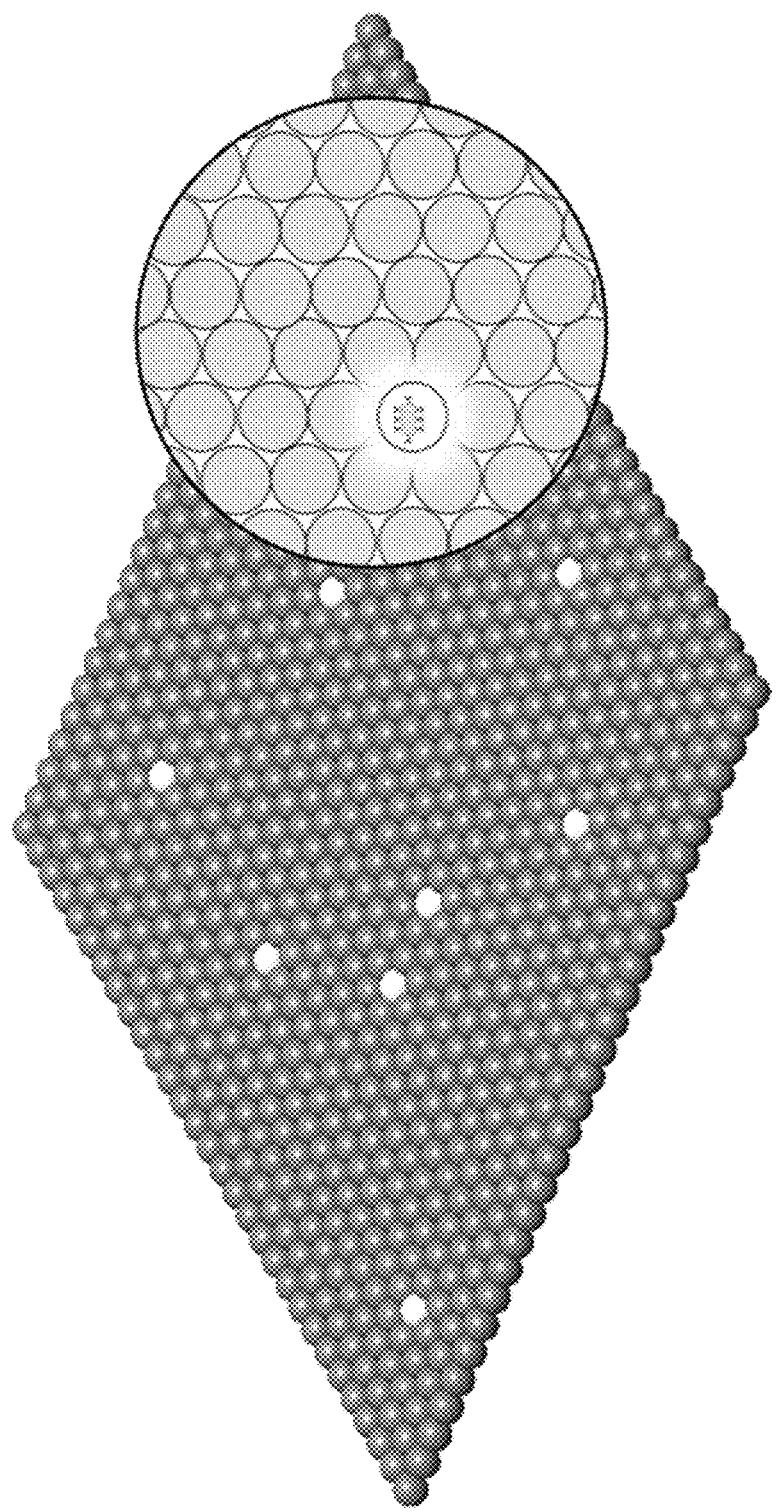
FIG. 3 is an illustration of a two-dimensional droplet array.
Figure 4:
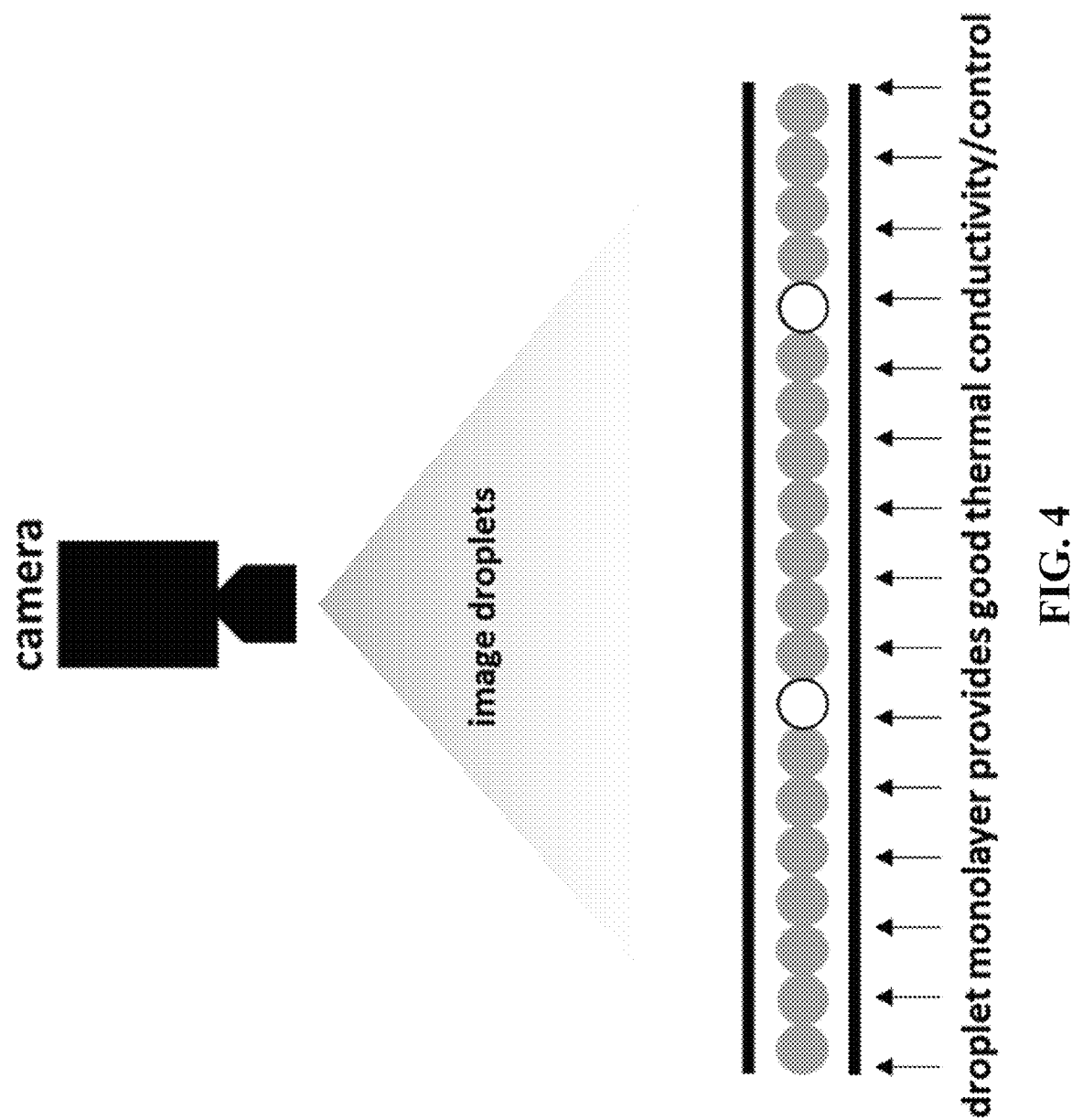
FIG. 4 is an illustration of a droplet monolayer being imaged by a camera. The droplet monolayer provides for good thermal conductivity and temperature control.
Figure 5:
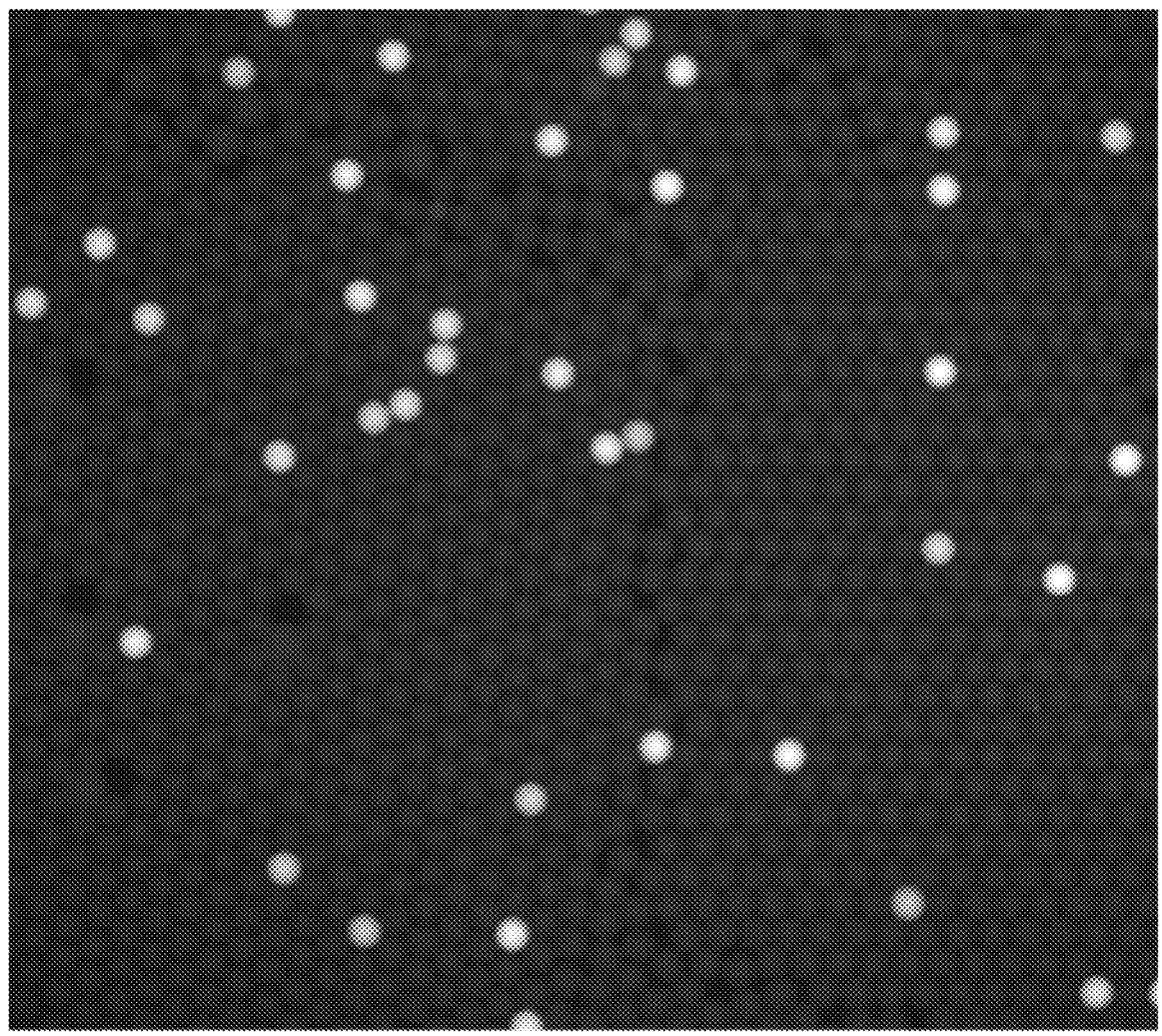
FIG. 5 is an image a droplet array containing *E. coli* cells.

Signal Detection. Once the droplets have been generated, they must be presented for analysis by an optical system, sensor, or sensor array. In a preferred embodiment, the droplets are presented in a two-dimensional array (FIGS. 3, 4, and 5) so that good thermal control can be maintained and the droplet signals can be measured simultaneously (at a single instance in time) for many droplets. In the droplets containing target cells, the reporter will produce a concentrated fluorescent signal that will rise above the background droplets that do not contain cells (FIGS. 3, 4, and 5). The concentrated signal of the droplet enables single cell identification in comparable time standard PCR techniques which are the gold standard for fast identification. In certain aspects the signal is detected by exciting a reduced reporter with a specific wavelength of light and collecting the band-pass-filtered, Stokes-shifted light with a camera as shown in FIG. 4. The advantage to use imaging techniques is that they can image a droplet array that remains stationary and can therefore easily be monitored over time. Cytometry based methods typically employ endpoint detection instead of real time detection because of the difficulty in keeping track of the moving droplets over time. Another advantage to imaging the array is that all the droplets experience the same reaction conditions at the time of analysis. Therefore, droplet signals can be compared at equivalent time points which is important since signals vary over time. With a cytometry approach, droplets pass by the detector at different times. Therefore, some droplets are incubated longer than others at the time of analysis. Finally, there may be different target cell species in the test sample. For each species, there may be an optimal droplet volume and dye concentration that maximizes signal at a particular time point. If an endpoint method is used, droplet volume and reporter concentrations do not need be controlled to the same degree because time can compensate for sub optimality and different species can be characterized universally within a single dye and droplet concentration.

Figure 8:
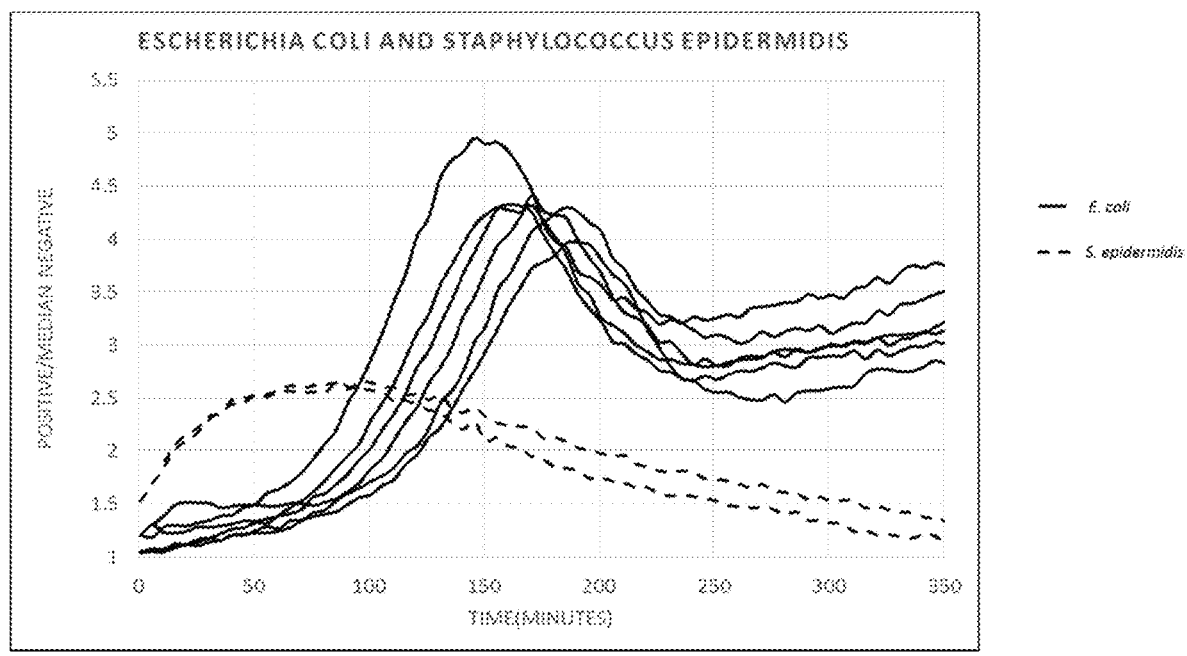
FIG. 8 illustrates multiple waveforms from an array comprising a multiple cell types (*E. coli* and *S. epidermis*) partitioned into microdroplets. The waveforms are clearly distinguishable.
Figure 9:
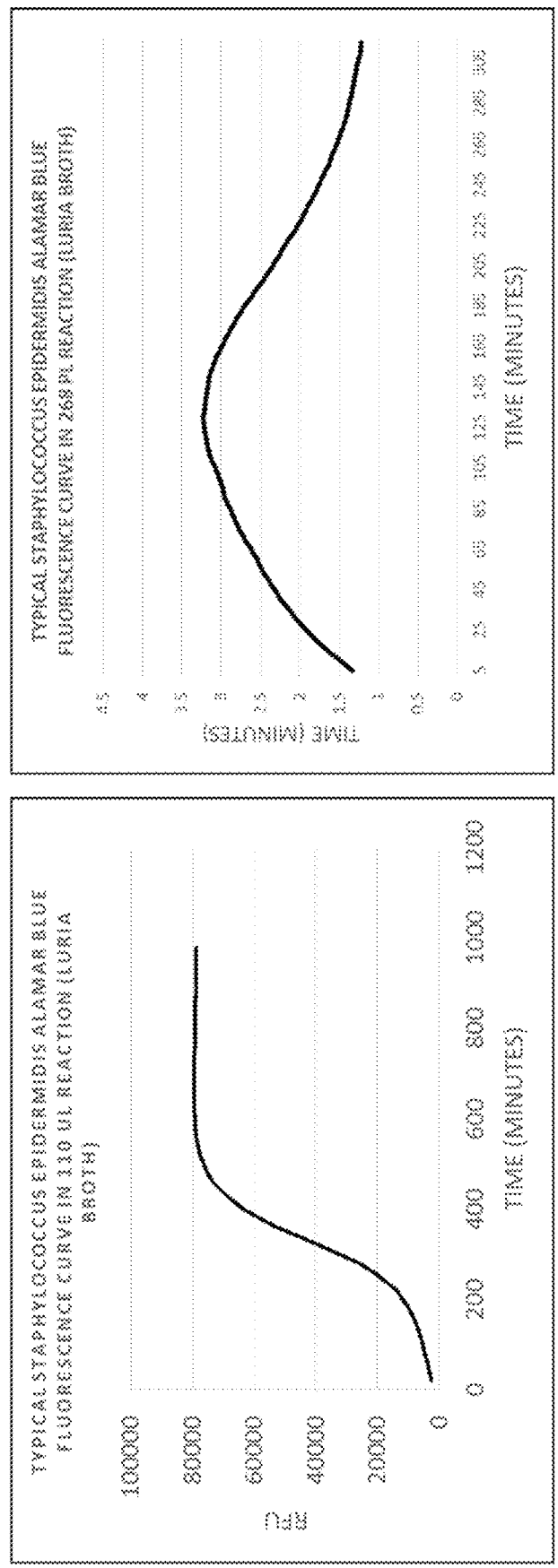
FIG. 9 provides a comparison of fluorescence relative to volume. The fluorescence waveform generated by a single bacterium incubated in pico-liter droplets rises much faster than in larger volumes, as expected, but also unexpectedly collapses due to a different redox potential in the picodroplet.

Multiplexing. The methods described herein include the specific identification of multiple cells from a single test sample. By compartmentalizing single cells into their own isolated droplet, competition for resources between cells is eliminated. Therefore, individual cells that would exist collectively as a minority in a bulk population, now have equal access to nutrients when compared to the majority population of cells which results in a higher sensitivity for low abundance cells in a sample with multiple cells types. The multiplexing limitations for this invention depend on the ability to differentiate viability signatures between different cell types. FIG. 8 is a schematic illustration showing two different cell types in the droplets and a graph of the fluorescent signals generated by two different bacterial species, E. coli and S. epidermidis, that were in the same test sample. Most methods for multiplexing require multiple dyes (fluorophores) which, in turn, require multiple sets of LEDs, excitation, and emission filters. Because the method described herein uses shape information rather than spectral information, the method can be used to multiplex many targets with a single dye requiring only one LED, emission filter, and excitation filter, thus simplifying the hardware needed to perform the analysis.

The preceding description and examples, as well as the figures are included to demonstrate particular aspects of the invention. It should be appreciated by those of skill in the art that the techniques disclosed in the description, examples, or figures represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

What is claimed:

1. A method for detecting and characterizing microbes in a sample, the method comprising:
   (a) isolating microbes from a sample, to form an isolated sample, wherein isolating the microbes comprises separating non-microbe cells, viruses, proteins, and nucleic acids from microbe cells;
   (b) dividing the sample into at least two sample portions and suspending a first sample portion in a first growth medium and suspending a second sample portion in a second growth medium, and each sample portion including a reporter, forming a first and a second sample mixture;
   (c) partitioning the first and second sample mixture forming first sample partitions and second sample partitions, wherein some of the first and second sample partitions have at most one microbial cell or microbial cell aggregate per partition;
   (d) incubating the partitions over time at a specific temperature or temperatures;
   (e) monitoring optical characteristics of the partitions during the incubation time, wherein the optical characteristics include the amount of optical signal produced by interaction of the reporter with the microbial cell or microbial cell aggregate in the partition;
   (f) constructing an optical signal waveform for each partition resulting in a partition waveform; and
   (g) comparing partition waveforms between the first and second sample partition waveforms and assessing the microbes based on partition waveform comparison, wherein the microbes are detected and characterized based on the comparison of the first and second waveforms from each sample portion.

2. The method of claim 1, further comprising classifying the microbial cell or microbial cell aggregate within each partition using the partition waveform shape.

3. The method of claim 2, wherein the classifying comprises comparing the waveforms of each sample to a library of stored waveforms.

4. The method of claim 1, wherein the partitions are droplets in an immiscible fluid.

5. The method of claim 4, wherein the immiscible fluid is a fluorocarbon comprising a fluorosurfactant.

6. The method of claim 4, further comprising arranging the droplets in a two-dimensional array monolayer.

7. The method of claim 6, wherein the two-dimensional array is a static two-dimensional array.

8. The method of claim 1, wherein partitioning the sample mixture is by using Laplace pressure gradients.

9. The method of claim 1, wherein partitioning the sample mixture is by using shear stress.

10. The method of claim 1, wherein monitoring optical characteristics of the partitions is performed using a camera.

11. The method of claim 1, wherein the reporter is a fluorescent dye.

12. The method of claim 1, wherein the reporter is resazurin, a resazurin-based dye, or a dye that is structurally related to resazurin.

13. The method of claim 1, where the reporter is tetrazolium, a tetrazolium-based dye, or a dye structurally related to tetrazolium.

14. The method of claim 1, wherein the monitoring optical characteristics of the partitions further comprises exciting the reporter using a light source.

15. The method of claim 14, wherein the light source is a light emitting diode (LED).

16. The method of claim 1, wherein the incubating of the partitions is at a constant temperature.

17. The method of claim 16, wherein the constant temperature is 37° C.

18. The method of claim 1, wherein the target cell within each partition is classified using the partition waveform shape.

19. The method of claim 1, wherein the second growth media comprising a nutrient or compound not present in the first growth media.

* * * * *